US010543289B2

(12) United States Patent
Taboada et al.

(10) Patent No.: US 10,543,289 B2
(45) Date of Patent: Jan. 28, 2020

(54) METHOD AND APPARATUS FOR RAPID STERILIZATION

(71) Applicants: John Taboada, San Antonio, TX (US); John Martin Taboada, San Antonio, TX (US)

(72) Inventors: John Taboada, San Antonio, TX (US); John Martin Taboada, San Antonio, TX (US)

( * ) Notice: Subject to any disclaimer, the term of this patent is extended or adjusted under 35 U.S.C. 154(b) by 145 days.

(21) Appl. No.: 15/805,111

(22) Filed: Nov. 6, 2017

(65) Prior Publication Data

US 2018/0071417 A1   Mar. 15, 2018

Related U.S. Application Data

(63) Continuation-in-part of application No. 15/489,705, filed on Apr. 17, 2017, now Pat. No. 9,808,546, which is a continuation-in-part of application No. 14/927,444, filed on Oct. 29, 2015, now Pat. No. 9,623,131.

(60) Provisional application No. 62/072,306, filed on Oct. 29, 2014, provisional application No. 62/513,846, filed on Jun. 1, 2017.

(51) Int. Cl.
*A61L 2/10* (2006.01)
*H01S 3/00* (2006.01)
*A61B 1/12* (2006.01)

(52) U.S. Cl.
CPC .............. *A61L 2/10* (2013.01); *H01S 3/005* (2013.01); *A61B 1/121* (2013.01)

(58) Field of Classification Search
USPC ....................................... 250/455.11, 454.11
See application file for complete search history.

(56) References Cited

U.S. PATENT DOCUMENTS

| 9,093,258 | B2 | 7/2015 | Stibich et al. | |
| 9,165,756 | B2 | 10/2015 | Stibich et al. | |
| 9,517,284 | B1 | 12/2016 | Stibich et al. | |
| 2006/0207431 | A1* | 9/2006 | Baca | A61L 2/0011 96/224 |
| 2008/0265179 | A1* | 10/2008 | Havens | A61L 2/10 250/492.1 |
| 2015/0008167 | A1* | 1/2015 | Shturm | C02F 1/001 210/85 |

* cited by examiner

*Primary Examiner* — Kiet T Nguyen
(74) *Attorney, Agent, or Firm* — Taboada Law Firm, PLLC; John M. Taboada

(57) ABSTRACT

Methods and systems for sterilizing a tools and equipment are disclosed, including using a UV source to generate a pulsed UV light within or exterior to an enclosure having a highly reflecting diffuse inner coated surface; and absorbing the pulsed light to sterilize. Other embodiments are described and claimed.

16 Claims, 1 Drawing Sheet

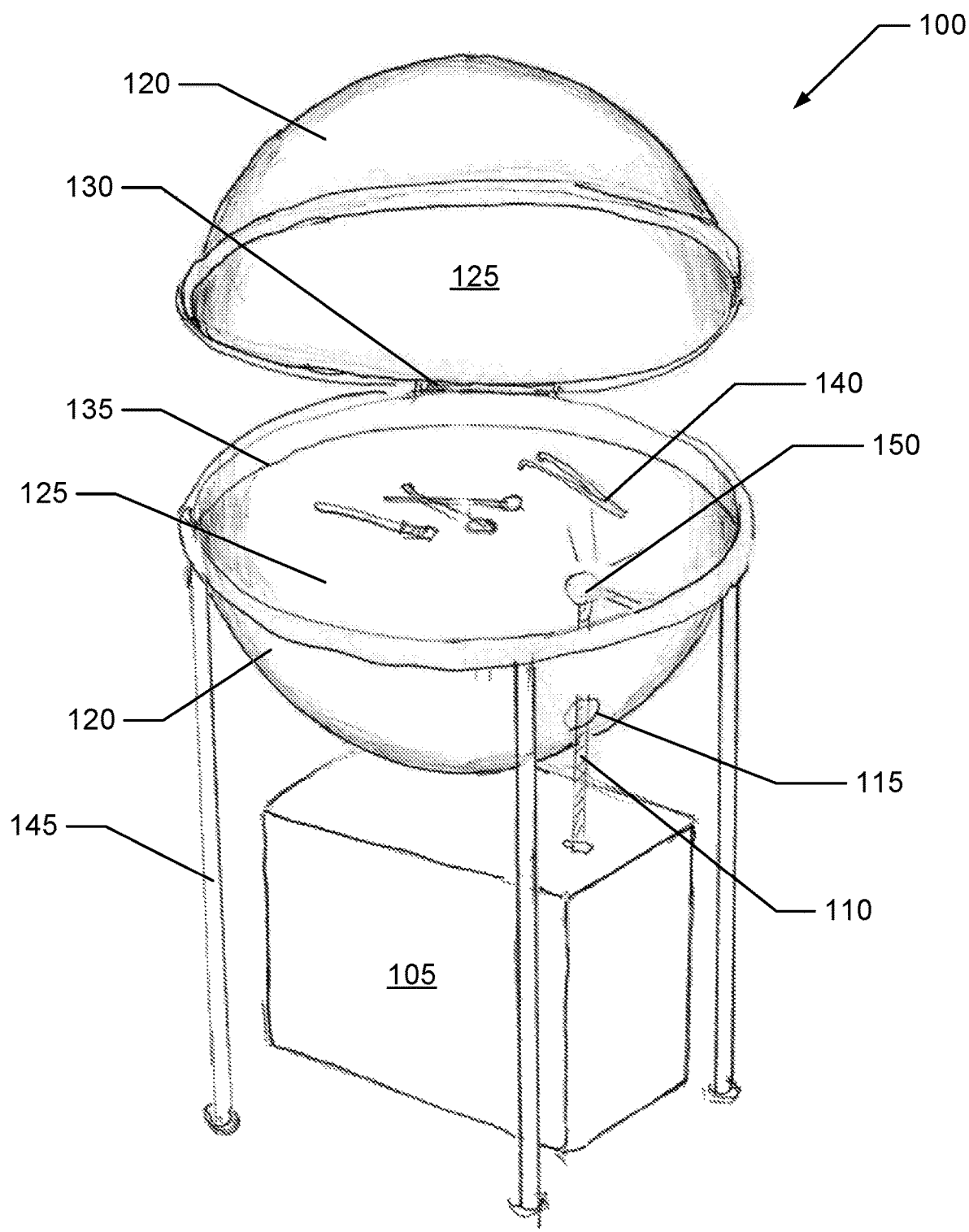

METHOD AND APPARATUS FOR RAPID STERILIZATION

I. CROSS REFERENCE TO RELATED APPLICATIONS

The application claims the benefit of the filing date of U.S. Provisional Patent Application Ser. No. 62/513,846, filed on Jun. 1, 2017, entitled "Method and Apparatus for Rapid Sterilization," the entire disclosure of which is hereby incorporated by reference into the present disclosure, and also is a continuation-in-part application of U.S. patent application Ser. No. 15/489,705, titled "Method and Apparatus for Rapid Sterilization of a Room", filed Apr. 17, 2017, the contents of which is hereby incorporated by reference, which is a continuation-in-part application of U.S. Pat. No. 9,623,131, titled "Method and Apparatus for Rapid Sterilization of Hazmat Suits, Surgical Instruments and the Like", filed Oct. 29, 2015, the contents of which is hereby incorporated by reference, which claims the benefit of the filing date of U.S. Provisional Patent Application Ser. No. 62/072,306, filed on Oct. 29, 2014, entitled "Method and Apparatus for Rapid Sterilization of Hazmat Suits, Surgical Instruments and the Like," the entire disclosure of which is hereby incorporated by reference into the present disclosure.

II. BACKGROUND

The invention relates generally to sterilization of tools and equipment. More particularly, the invention relates to an innovative method and apparatus for the rapid sterilization of tools and equipment exposed to hazardous infectious agents, harmful bacteria, and pathogens.

III. SUMMARY

In one respect, disclosed is an apparatus for sterilizing, comprising: an enclosure having a highly reflecting diffuse inner coated surface; and a UV source within the enclosure.

In another respect, disclosed is a method for sterilizing: using a UV source to generate a pulsed UV light within an enclosure having a highly reflecting diffuse inner coated surface; and absorbing the pulsed light to sterilize.

In a further respect the UV source may be located exterior to the enclosed surface with a beam from the source projected into the interior of the enclosure Numerous additional embodiments are also possible.

IV. BRIEF DESCRIPTION OF THE DRAWINGS

Other objects and advantages of the invention may become apparent upon reading the detailed description and upon reference to the accompanying drawings.

FIG. 1 is a schematic diagram illustrating an apparatus for the rapid sterilization of materials and tools, in accordance with some embodiments.

While the invention is subject to various modifications and alternative forms, specific embodiments thereof are shown by way of example in the drawings and the accompanying detailed description. It should be understood, however, that the drawings and detailed description are not intended to limit the invention to the particular embodiments. This disclosure is instead intended to cover all modifications, equivalents, and alternatives falling within the scope of the present invention as defined by the appended claims.

V. DETAILED DESCRIPTION

One or more embodiments of the invention are described below. It should be noted that these and any other embodiments are exemplary and are intended to be illustrative of the invention rather than limiting. While the invention is widely applicable to different types of systems, it is impossible to include all of the possible embodiments and contexts of the invention in this disclosure. Upon reading this disclosure, many alternative embodiments of the present invention will be apparent to persons of ordinary skill in the art.

In some embodiments, an apparatus 100 for the rapid sterilization of materials and tools comprises a high power Excimer laser 105 using KrF pump media emitting nanosecond UV light pulses at 248 nm. This pulsed UV light has very efficient antibiotic characteristics. The laser beam 110 from this laser source enters through an aperture 115 of a substantially spherical enclosure 120. The substantially spherical enclosure comprises a highly reflecting diffuse inner coated surface 125, for example Spectralon. In some embodiments, the enclosure may vary from spherical (cylinder, box etc.). In some embodiments, as illustrated in FIG. 1, the substantially spherical enclosure 120 comprises a hinge 130 which allows for the opening of the substantially spherical enclosure. Within the enclosure, a UV transmissive support structure 135, such as a UV Grade Fused Silica plate may be used, to hold the tools and equipment 140 in the central region of the enclosure. The substantially spherical enclosure 120 may be supported by legs 145, which may also serve to enclose the laser 105 in the space below the substantially spherical enclosure.

In some embodiments, the laser beam 110 may be directed directly onto the highly reflecting diffuse inner coated surface 125. In other embodiments, the laser beam 110 may be directed onto a substantially isotropically scattering optical element 150, such as spherically scattering spheres. Because the UV light pulses are brought into spherically scattering sources within the substantially spherical enclosure having a highly reflecting diffuse inner coated surface, the entire cavity will be uniformly illuminated with the UV light pulses. The tools and equipment 140 will be instantly uniformly illuminated and rapidly sterilized and sanitized.

In other embodiments, the laser comprises a fourth harmonic q-switched Nd:YAG solid state laser, a fourth harmonic mode locked Nd:YAG solid state laser, a fourth harmonic q-switched Nd:YLF solid state laser, a fourth harmonic mode locked Nd:YLF solid state laser, a fourth harmonic q-switched Nd:YVO$_4$ solid state laser, and/or a fourth harmonic mode locked Nd:YVO$_4$ solid state laser. All of these laser sources are capable of generating short pulses of far UV light which maximizes the lethality of the radiation acting on the pathogenic organisms. Depending on the exact laser source, the wavelength may range from about 200 nm to about 320 nm and the pulsed laser beam may comprise nanosecond to picosecond light pulses.

In some embodiments, the scattering optical element 150 comprises a spherically scattering sphere which isotropically illuminates the interior of the substantially spherical enclosure with sterilizing pulsed UV light to rapidly sterilize the tools and equipment. The spherically scattering sphere comprises a hollow UV grade fused silica bulb filled with either solid or hollow UV grade fused silica spheres. The solid or hollow UV grade fused silica spheres scatter the incident laser radiation in a substantially isotropic manner.

In an alternate embodiment, the scattering optical element 150 comprises a fiber optic bundle, i.e., a fused bundle of individual fiber optic filaments. In this embodiment, the pulsed UV light is projected radially outward from the fiber optic bundle forming an omnidirectional, substantially planar sheet of UV light. An example of one such fiber optic bundle was disclosed in U.S. Pat. No. 5,898,809 issued to J. Taboada, et al., which is herein incorporated by reference.

In alternate embodiments, other UV sterilization light sources may be used, such as placing xenon or mercury vapor lamps within the substantially spherical enclosure.

In alternate embodiments the enclosure is rectangular, square, or some other cuboid shape.

The previous description of the disclosed embodiments is provided to enable any person skilled in the art to make or use the present invention. Various modifications to these embodiments will be readily apparent to those skilled in the art, and the generic principles defined herein may be applied to other embodiments without departing from the spirit or scope of the invention. Thus, the present invention is not intended to be limited to the embodiments shown herein but is to be accorded the widest scope consistent with the principles and novel features disclosed herein.

The benefits and advantages that may be provided by the present invention have been described above with regard to specific embodiments. These benefits and advantages, and any elements or limitations that may cause them to occur or to become more pronounced are not to be construed as critical, required, or essential features of any or all of the claims. As used herein, the terms "comprises," "comprising," or any other variations thereof, are intended to be interpreted as non-exclusively including the elements or limitations which follow those terms. Accordingly, a system, method, or other embodiment that comprises a set of elements is not limited to only those elements, and may include other elements not expressly listed or inherent to the claimed embodiment.

While the present invention has been described with reference to particular embodiments, it should be understood that the embodiments are illustrative and that the scope of the invention is not limited to these embodiments. Many variations, modifications, additions and improvements to the embodiments described above are possible. It is contemplated that these variations, modifications, additions and improvements fall within the scope of the invention as detailed within the following claims.

The invention claimed is:

1. An apparatus for sterilizing comprising:
   an enclosure having a highly reflecting diffuse inner coated surface; and
   a UV source within the enclosure, wherein the UV source comprises a pulsed laser beam emitted from a laser outside of the enclosure.

2. The apparatus of claim 1, wherein the laser comprises at least one of a KrF Excimer laser, a fourth harmonic q-switched Nd:YAG solid state laser, a fourth harmonic mode locked Nd:YAG solid state laser, a fourth harmonic q-switched Nd:YLF solid state laser, a fourth harmonic mode locked Nd:YLF solid state laser, a fourth harmonic q-switched Nd:YVO4 solid state laser, and a fourth harmonic mode locked Nd:YVO4 solid state laser.

3. The apparatus of claim 1, further comprising a scattering optical element configured to intercept and substantially isotropically scatter the radiation of the pulsed laser beam.

4. The apparatus of claim 3, wherein the scattering optical element comprises a hollow fused silica bulb filled with fused silica spheres.

5. The apparatus of claim 4, wherein the fused silica spheres are solid and/or hollow.

6. The apparatus of claim 3, wherein the scattering optical element comprises a fiber optic bundle.

7. The apparatus of claim 1, wherein the pulsed laser beam comprises a wavelength ranging between about 200 nm to about 320 nm.

8. The apparatus of claim 1, wherein the pulsed laser beam comprises nanosecond or picosecond light pulses.

9. A method for sterilizing comprising:
   using a UV source to generate a pulsed UV light within an enclosure having a highly reflecting diffuse inner coated surface, wherein the UV source comprises a pulsed laser beam emitted from a laser outside of the enclosure; and
   absorbing the pulsed light to sterilize.

10. The method of claim 9, wherein the laser comprises at least one of a KrF Excimer laser, a fourth harmonic q-switched Nd:YAG solid state laser, a fourth harmonic mode locked Nd:YAG solid state laser, a fourth harmonic q-switched Nd:YLF solid state laser, a fourth harmonic mode locked Nd:YLF solid state laser, a fourth harmonic q-switched Nd:YVO4 solid state laser, and a fourth harmonic mode locked Nd:YVO4 solid state laser.

11. The method of claim 9, further comprising a scattering optical element configured to intercept and substantially isotropically scatter the radiation of the pulsed laser beam.

12. The method of claim 11, wherein the scattering optical element comprises a hollow fused silica bulb filled with fused silica spheres.

13. The method of claim 12, wherein the fused silica spheres are solid and/or hollow.

14. The method of claim 11, wherein the scattering optical element comprises a fiber optic bundle.

15. The method of claim 9, wherein the pulsed laser beam comprises a wavelength ranging between about 200 nm to about 320 nm.

16. The method of claim 9, wherein the pulsed laser beam comprises nanosecond or picosecond light pulses.

* * * * *